United States Patent
Jung, Jr.

(10) Patent No.: US 7,066,950 B2
(45) Date of Patent: Jun. 27, 2006

(54) VAPOR THERAPY TREATMENT DEVICE AND METHOD FOR GENERATING THERAPEUTIC VAPOR TREATMENT

(75) Inventor: Herbert C. Jung, Jr., Spartanburg, SC (US)

(73) Assignee: Cherokee Products, Inc., Gaffney, SC (US)

( * ) Notice: Subject to any disclaimer, the term of this patent is extended or adjusted under 35 U.S.C. 154(b) by 236 days.

(21) Appl. No.: 10/284,813

(22) Filed: Oct. 31, 2002

(65) Prior Publication Data

US 2004/0088030 A1 May 6, 2004

(51) Int. Cl.
*A61F 7/00* (2006.01)

(52) U.S. Cl. .................................. 607/114; 607/96
(58) Field of Classification Search .............. 607/96, 607/98–114, 108–112
See application file for complete search history.

(56) References Cited

U.S. PATENT DOCUMENTS

| | | | |
|---|---|---|---|
| 2,973,762 A | | 3/1961 | Koenig |
| 3,848,281 A | | 11/1974 | Mathews |
| 5,366,491 A | | 11/1994 | Ingram et al. |
| 5,375,278 A | | 12/1994 | Van Winkle et al. |
| 5,456,704 A | * | 10/1995 | Kilcullen ............ 607/111 |
| 5,584,086 A | | 12/1996 | Van Winkle et al. |
| 5,630,961 A | | 5/1997 | Salee |
| 6,119,855 A | * | 9/2000 | Yeager et al. ......... 206/213.1 |

OTHER PUBLICATIONS

Material Safety Data Sheet for LITE–DRI® Absorbent (MSD–006) for the New Pig Corporation, Tipton, PA., pp. 1& 2.

http://www.newpig.com/Npdoc/browse/pp.i html?productId=PLP201, PIG® LiteDri® Absorbent, entitled LITE–DRI® Absorbent absorbs 3 times more than clay!.

http://ww.jm.com/insulation/faqs res/019.html, JM FAQ—entitled "What are the differences (pros and cons) between fiber glass and cellulose insulation?".

http://ww.../ppDocPage.jhtm;?url=%2FNPd oc%2Fcontent%2F1587345%2FPLP201.ht.New Pig Leak & Spill Absorbents, entitled Product Data Sheet.

http://www.ianr.unl.edu/pubs/housing/nf40.htm, Insulation Information for Nebraska Homeowners, NF 91–40, entitled "Insulation Information for Nebraska Homeowners".

Zanders USA, Bulletin 2, entitled "Ambient Control and Paper Stability", pp. 5–7.

* cited by examiner

*Primary Examiner*—Roy D. Gibson
*Assistant Examiner*—Aaron Roane
(74) *Attorney, Agent, or Firm*—Dority & Manning, P.A.

(57) ABSTRACT

A vapor therapy treatment device and method for generating a therapeutic vapor is disclosed. The vapor therapy treatment device includes a cushion having an inner space with water-absorbing material therein. The cushion includes a cover having an outer surface and a vapor permeable pouch associated with or connected to the cushion. The pouch is adapted for receiving, retaining, and subsequently releasing vapor therapy materials or compositions. Upon heating of the water-absorbing material, water vapor is released. Released water vapor may combine with vapor therapy materials and compositions to form a gaseous therapeutic vapor. The heated cushion can be applied to the face and/or nose of a user, facilitating inhalation by a user of therapeutic vapors released from the device.

6 Claims, 4 Drawing Sheets

VAPOR THERAPY TREATMENT DEVICE AND METHOD FOR GENERATING THERAPEUTIC VAPOR TREATMENT

BACKGROUND OF THE INVENTION

Many people suffer from sinus headaches, lung congestion, asthma, or related respiratory problems. Various methods and apparatus have been developed to provide relief from symptoms associated with such conditions.

Steam-generating devices, for example, vaporize water into the air for inhalation. Unfortunately, existing steam-generating devices may have significant drawbacks. Steam-generating devices for the home usually are relatively expensive. Furthermore, maintaining a steam-generating device in the home requires frequent maintenance, including periodic re-filling of the device with water. Electrical steam generating apparatus requires costly electrical power to operate. Many steam-generating devices are limited with regard to portability. Such devices typically must produce much more total water vapor than is actually ingested by the patient. It is sometimes necessary to fill an entire room with water vapor before achieving an ambient vapor concentration sufficient to provide desirable effects upon a user.

Some inhalation devices have been designed for placement directly into the mouth, thereby facilitating respiratory treatment by direct inhalation of therapeutic agents. However, direct methods for administering therapeutic agents also have disadvantages. Many such inhalation devices are not adapted for use with moist heat or steam. For many users, however, application of heated water vapor assists in relieving symptoms relating to such illnesses.

U.S. Pat. No. 5,630,961 to Salee is directed to a thermal storage composition activated by exposure to microwave energy. The composition comprises a mixture of at least two impregnated powders wherein a first powder is calcium silicate, and a second powder is calcium silicate impregnated with a phase-change material. Another patent, U.S. Pat. No. 5,366,491 pertains to a microwave-activated moist heat apparatus for the body. U.S. Pat. No. 5,375,278 is directed to a therapeutic pillow having a removable washable outer sleeve. The pillow has a bag-like cover filled with granular material having a water content in the range of 5% to 25% by weight. U.S. Pat. No. 5,584,086 is related to the patent described above (i.e. the U.S. Pat. No. 5,375,278) and further describes a therapeutic pillow having a bag-like cover filled with natural granular material.

U.S. Pat. No. 3,848,281 is directed to a foam rubber cushion suitable for use as an infant headrest or the like. U.S. Pat. No. 2,973,762 describes a steam cloth that is useful during facial treatments in a barber shop or a beauty salon.

What is needed is a device and method for generating and radiating heated water vapor to the facial area of a person. An apparatus that is capable of retaining and subsequently releasing heated water vapor in combination with therapeutic agents for contact with the facial area of a user, and for inhalation by a user, would be very desirable.

SUMMARY OF THE INVENTION

The vapor therapy treatment device provides a cushion having an inner space containing water-absorbing material. A vapor permeable cover encloses the water absorbing material. A vapor permeable pouch is associated with the cushion. The pouch is adapted for receipt, retention and subsequent release of vapor therapy materials. When water is absorbed within the water absorbing material, subsequent application of energy to the cushion results in release of vapor therapy materials from the vapor permeable pouch.

In one embodiment of the invention a fastener is provided for attaching the pouch to the cover of the cushion. The fastener may be of various types, including for example hook and loop materials, snap-type, buttons, zippers, and the like. In one embodiment of the invention the fastener includes a first component configured for attachment to the vapor permeable pouch and a second component adapted for attachment to the outer surface of the cover. The first and second components are adapted to interconnect the vapor permeable pouch to the cover, while also facilitating selective disengagement of the pouch from the cover.

A method for producing therapeutic vapors is provided. In the method, the water absorbing material takes in water, and subsequently water is released upon heating of the water absorbing material. In the method, a pouch is positioned adjacent the outer surface of the vapor permeable cover. The pouch is adapted to hold a vapor therapy material or composition. The vapor therapy materials within the pouch are contacted by heated water vapor to generate therapeutic vapors. The therapeutic vapors may be applied to the facial area of a user. In one method, the therapeutic vapor is provided for inhalation by a user.

BRIEF DESCRIPTION OF THE DRAWINGS

A full and enabling disclosure of this invention, including the best mode shown to one of ordinary skill in the art, is set forth in the specification. The following Figures illustrate the invention.

DETAILED DESCRIPTION OF THE INVENTION

Figure 1:
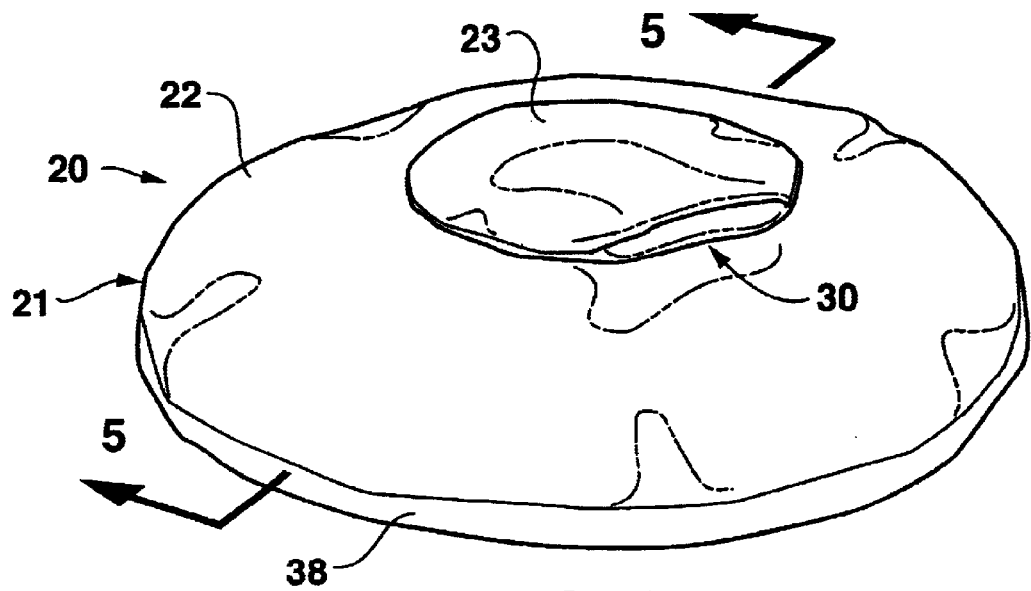
FIG. 1 is a perspective view of an exemplary present vapor therapy treatment device including a pouch attached to a larger cushion.

Reference now will be made to the embodiments of the invention, one or more examples of which are set forth below. Each example is provided by way of explanation of the invention, not as a limitation of the invention. In fact, it will be apparent to those skilled in the art that various modifications and variations can be made in this invention without departing from the scope or spirit of the invention.

A vapor therapy treatment device includes a cushion 20 of cotton flannel material forming vapor permeable cover 21. A vapor permeable pouch 23 having an opening 30 is releasably attached to the outer surface 22 of the vapor permeable cover 21.

Figure 2:
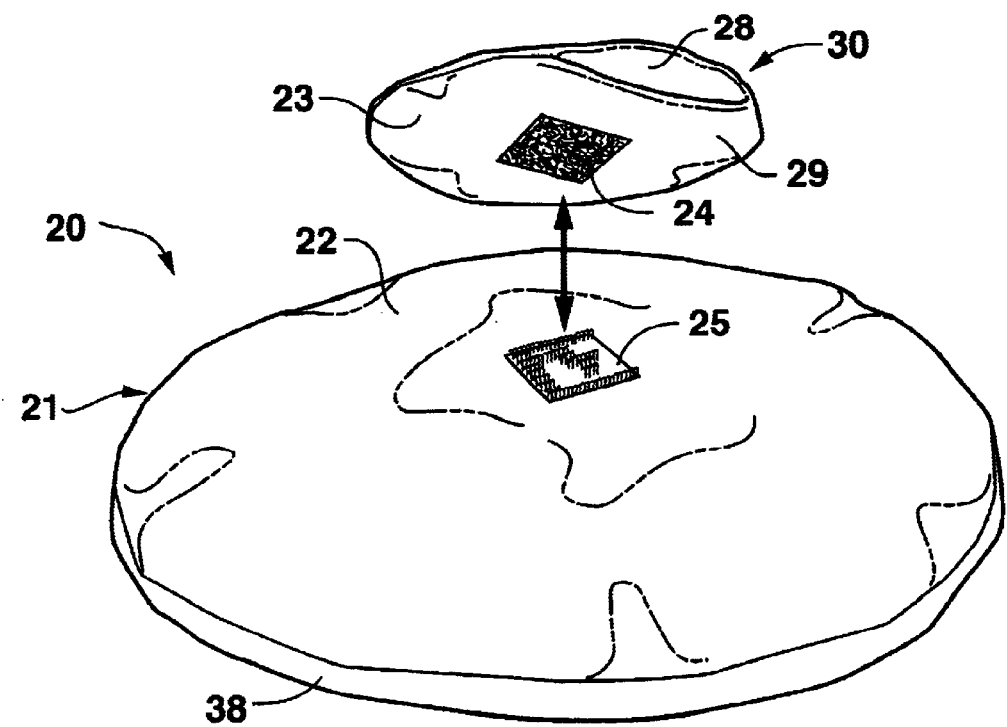
FIG. 2 shows a further perspective view of an exemplary present vapor therapy treatment device in which the pouch is disengaged from the cushion.

In the embodiment of the invention shown in FIGS. 1–2, the vapor permeable pouch 23 is selectively detachable from the outer surface 22 of the vapor permeable cover 21. FIG. 2 employs a fastener which includes a first component 24 and a second component 25 which mate to each other. In the particular embodiment of FIG. 2, the respective first and second components 24–25 comprise a hook and loop type fastening system. The hook portion of the fastener is the second component 25, while the loop portion of the fastener is the first component 24. In other applications of the invention, however, the loop portion of the fastener could be provided as second component 25 upon the outer surface 22 of the vapor permeable cover 21. In such an embodiment, the hook portion of the fastener could reside upon the vapor permeable pouch 23. Thus, in either embodiment, it is possible to disengage and re-attach the pouch 23 to the vapor permeable cover 21, as needed.

Other embodiments of the invention may employ other types of fasteners. For example, snap-type fasteners, buttons, zippers, or other mechanical means can be used to releaseably engage the vapor permeable pouch 23 to the vapor permeable cover 21. The invention is not limited to any particular means of engaging or disengaging the vapor permeable pouch 23 to the vapor permeable cover 21.

Figure 5:
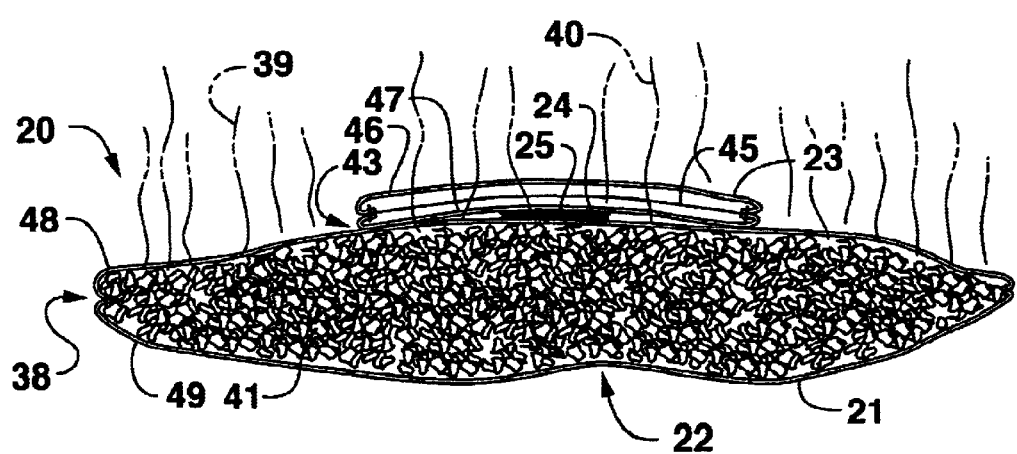
FIG. 5 shows a cross-section taken along line 5—5 of FIG. 1 revealing the transmission of heated water vapor through the vapor permeable cover and into the pouch, causing release of therapeutic vapors from the pouch.

The cushion 20 includes vapor permeable cover 21 enclosing water absorbing material 41 (see cross-sectional view along line 5—5 in FIG. 5). In the use of the invention, the water absorbing material 41 is capable of uptake or adsorption of water at ambient temperatures. Thus, water is retained within the water absorbing material 41 at ambient temperatures.

In FIG. 5, the top panel 48 and bottom panel 49 are joined by stitching at seam 38 to form the vapor permeable cover 21. The vapor permeable cover 21 encloses water absorbing material 41 which upon being heated by an energy source, such as microwave energy, causes water vapor 39, 40 to permeate through top panel 48.

The vapor permeable pouch 23 comprises a first panel 46 attached to a second panel 47 along seam 43. The vapor permeable pouch 23 includes an outside surface 29 and an inside surface 28 (see FIG. 4).

The cushion 20 contains water-absorbing material 41 which, when heated, releases water vapor 39 through the top panel 48 and through the second panel 47 of the vapor permeable pouch 23. This causes vapor therapy materials 35 residing within absorption area 45 of the vapor permeable pouch 23 to become airborne as therapeutic vapor 40.

Method of Use

Figure 6:
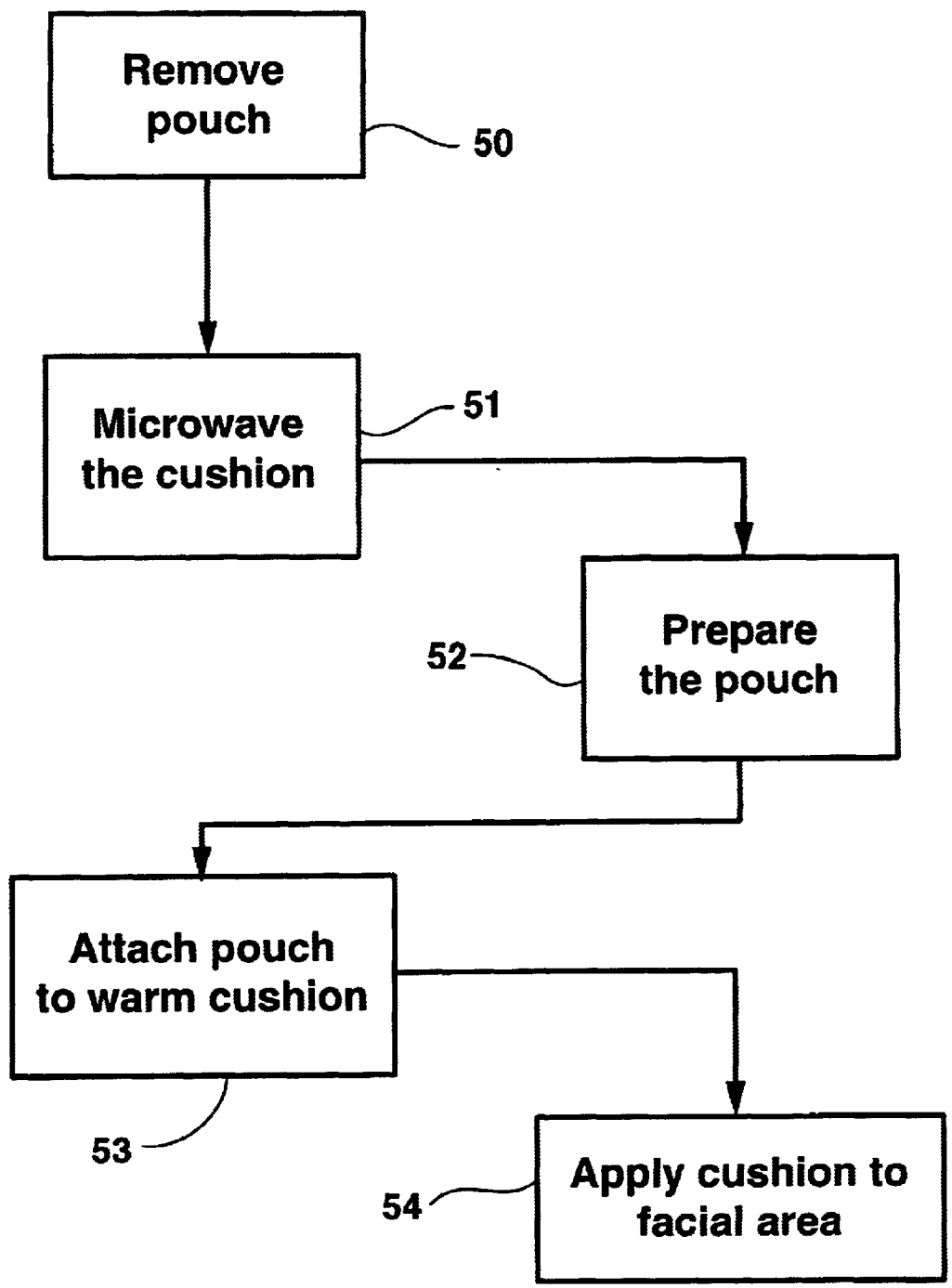
FIG. 6 is a schematic diagram showing one method of practicing the invention to produce a therapeutic vapor for application to the facial area of a user.

FIG. 6 is a schematic diagram showing one method of practicing the invention. Step 50 includes removing the vapor permeable pouch 23 from the cushion 20. Step 50 is unnecessary if the pouch 23 is already disengaged, as for example as shown in FIG. 2. It is usually undesirable to allow the vapor permeable pouch 23 to be subjected to microwave energy.

Figure 3:
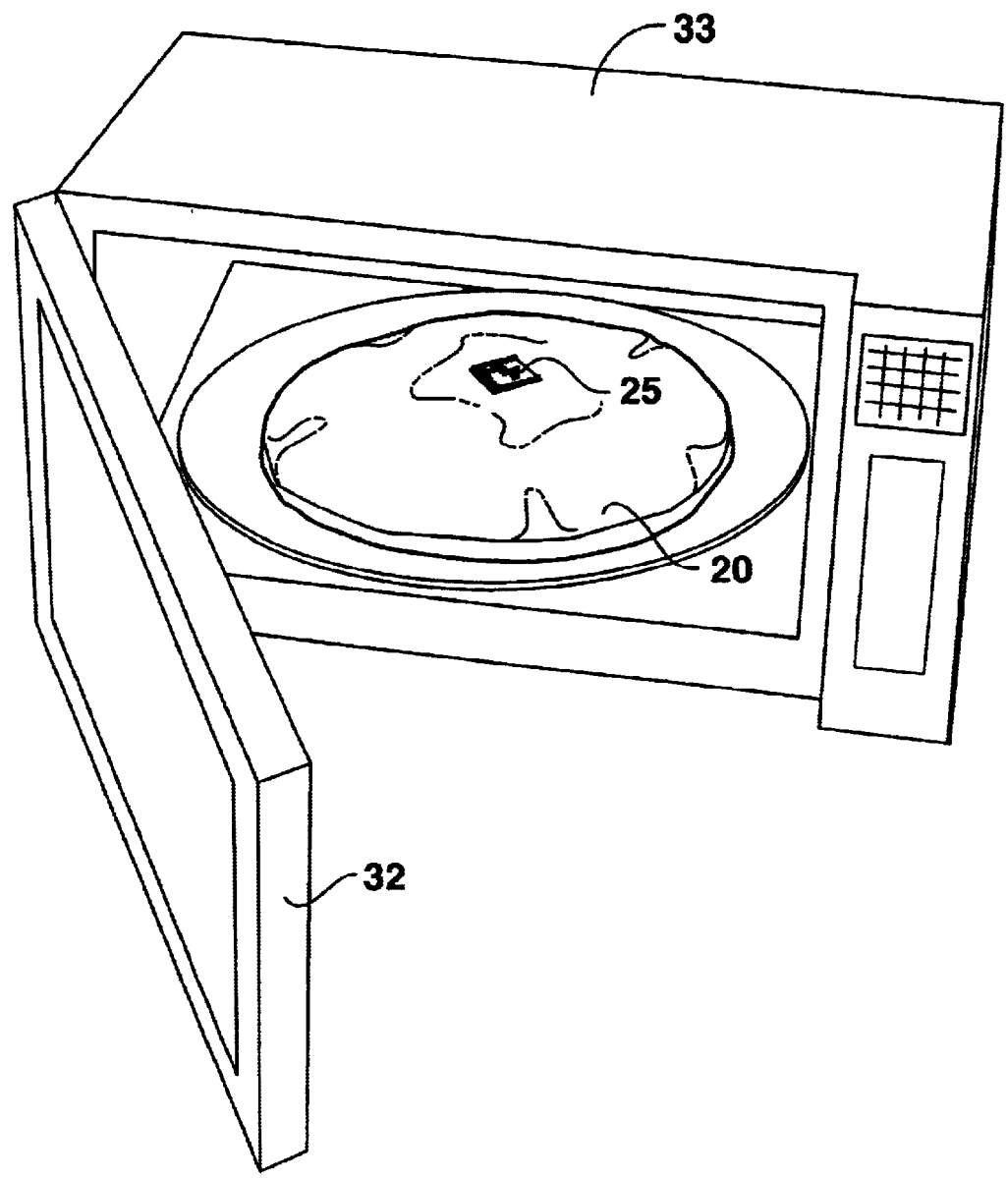
FIG. 3 illustrates one step in the method of the invention whereby an exemplary cushion having a water absorbing material therein is placed within a microwave oven and subjected to microwaves for a period of time, in accordance with present subject matter.

In one embodiment of the invention, in step 51, microwave energy is applied to the cushion 20 by placing the cushion 20 within a microwave oven 33 (FIG. 3). In other embodiments of the method, alternative sources of energy can be applied to the water absorbing material, as further discussed herein. However, a desirable and preferred method of generating water vapor release is to apply microwaves to the water absorbing material 41. The cushion 20 (without a pouch 23) is placed within the microwave oven 33, and the door 32 is closed. The cushion 20 is subjected to microwave heating for a period of time which varies between about 45 seconds and about 2 minutes, depending upon the amount of heat the user desires to apply in the particular application, and the power output of the microwave oven 33. Additional time variations may be practiced within the present subject matter, as determined by the user for their individual comfort level. Once the cushion 20 has been heated, the cushion 20 is removed from the microwave oven 33.

Alternatively, the cushion 20 may be heated while in an automobile by applying the cushion 20 to car seats which have automatic heat control or have received a significant amount of sunlight upon their surface. In other applications, the cushion 20 may be heated by placing it near a source of radiant heat, such as a fireplace, stove, heater, or furnace. In some applications, the cushion 20 may be placed in a clothing dryer and circulated within the dryer to heat the cushion 20. In yet another embodiment of the invention, liquid water may be wiped upon the outer surface 22 of the vapor permeable cover 21 prior to heating the cushion 20 to supplement or boost water vapor release.

Figure 4:
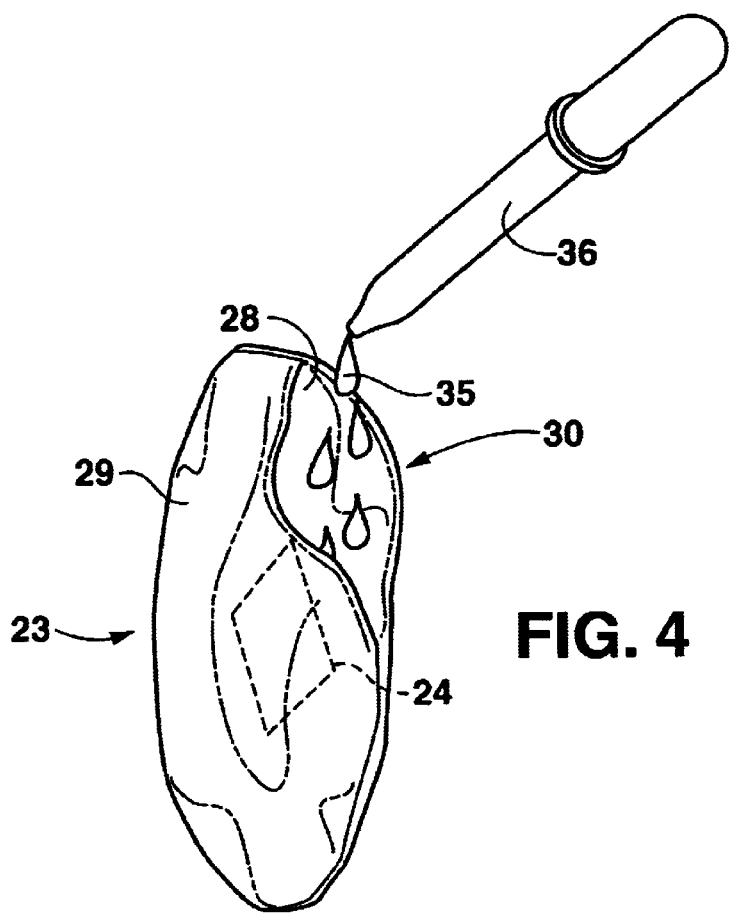
FIG. 4 displays one method of application of a vapor therapy material or composition to a vapor permeable pouch.

In a next step 52, the vapor permeable pouch 23 is prepared by applying vapor therapy materials 35 (also described herein as compositions) into or upon the vapor permeable pouch 23. In some embodiments of the invention, step 52 involves applying a vapor therapy material 35 which is a liquid upon an inside surface 28 of the vapor permeable pouch 23 (see FIG. 4). In the embodiment of the vapor permeable pouch 23 shown in FIG. 4, a dropper 36 is used to apply vapor therapy material 35 which is a liquid upon the inside surface 28 of the vapor permeable pouch 23. The vapor therapy material 35 may be absorbed upon the inside surface 28. Typically, the vapor therapy material 35 is applied to the vapor permeable pouch 23 while the pouch 23 is disengaged from the vapor permeable cover 21, as shown in FIG. 4.

Other applications of the invention may employ vapor therapy materials 35 which are solid, semi-solid, or flowable. In such applications, the materials 35 could be applied with a cotton swab or other wiping device upon outside surface 29 or inside surface 28 of the vapor permeable pouch 23.

Some applications of the invention employ more than one variety of vapor therapy materials 35. That is, two or more types of vapor therapy materials 35 may be used at one time in the course of one treatment. Some applications of the invention may employ non-flowable solid particles such as potpourri or aromatherapy materials, for example.

In step 53, the vapor permeable pouch 23 which has been prepared according to step 52 is applied to the warmed cushion 20. This may occur after the cushion 20 has received microwave energy, thereby allowing the water absorbing material 41 within the cushion 20 to absorb heat.

Once the vapor permeable pouch 23 has been applied to the warm cushion 20 as in step 53, the cushion 20 may be applied to the facial area of a user as in step 54 of FIG. 6. Vapor therapy materials 35 are released from the vapor permeable pouch 23 with water vapor as gaseous therapeutic vapors 40 (see FIG. 5). When a person places the heated cushion 20 upon or near his or her face, the gaseous therapeutic vapor 40 becomes available for contact with the user. The user then may breathe the therapeutic vapor 40 through his or her mouth or nose. In other applications, the vapor 40 may provide benefits by opening pores and soothing the user's skin in the facial/neck area.

After a period of time, a user may renew the treatment by re-heating the cushion 20. This involves removing the pouch 23 from the cover 21, heating again the water absorbing material 41, and re-applying the pouch 23 to the cover 21. The pouch 23 also may receive once more vapor therapy materials 35 if needed or desired.

The therapeutic vapor 40 which contains heated water vapor may open up sinus cavities and supply needed respiratory relief to a user. In other applications of the invention, the cushion 20 may be applied to other body parts for pain relief or heat therapy.

Additional Detailed Description

The vapor therapy treatment device of the invention may be used for relief of sinus pressure headaches, nasal itch, allergies, tension headaches, muscle pain, joint pain, backaches and the like. The cushion 20 is particularly useful in the relief of sinus headaches and related respiratory illnesses. The generation of heated water vapor without the necessity of adding liquid water to the device is a significant advantage in the practice of the invention.

In one embodiment of the invention, the vapor permeable cover 21 is comprised of cotton flannel, which is particularly well adapted for skin comfort. The fiber of the flannel may be non-toxic and unscented. One flannel that is particularly useful in the application of the invention is "clothing grade" flannel, including for example middleweight flannel. Such flannel may be obtained from various U.S. manufacturers, including Marcus Brothers Fabric Company, Benatex Fabric Company, and Timeless Treasures Company. In one particular embodiment, a one-layer exterior flannel sheet is used. The flannel sheet may be seamed or stitched by commercial sewing machines in the manufacture of the cushion.

The water absorbing material 41 employed in the invention may include essentially any material capable of uptake of liquid or gaseous water, including material that adsorbs water from the air. Hygroscopic materials which seek moisture equilibrium with the atmosphere are particularly useful. Cellulose, for example, may be used as a water absorbing material 41 in the application of the invention. The exposure of cellulose to relative humidity causes cellulose to either swell or shrink, depending upon the relative humidity.

One material which has proved particularly useful in the application of the invention is a water absorbing material 41 is a cellulosic material manufactured and marketed by the Pig Corporation known as PIG® Lite-Dri® Absorbent. This absorbent is available in eight-gallon bags and is light gray in color. This product (item number PLP201) is distributed by the PIG Corporation, 1 Pork Avenue, Tipton, Pa. 16684-0304 (online products catalog at http://newpig.com). This product is a non-selective loose absorbent cellulose which is said to be capable of absorbing and containing oils and other fluids. The Lite-Dri® product is comprised of recycled newsprint (cellulose). Furthermore, a small amount of mineral oil, typically less than about 1%, is provided in the product. The mineral oil fraction functions primarily to control dust. The mineral oil acts as a binding agent with the cellulose. The Lite-Dri® product typically is provided in granular or pellet form, and tends to be highly absorptive of various types of materials. The Lite-Dri® product absorbs water vapor from the air at ambient temperatures.

Various vapor therapy materials 35 may be applied in the practice of the invention. In some applications, the materials 35 include inhalation agents such as mentholated vapor products. In other applications, aromatherapy products and herbs, leaves, or floral potpourri may be used. In some applications, the vapor therapy compositions are scented, while in other applications they are unscented.

Various "over-the-counter" mentholatum products such as Vicks® Vapo-Rub®, for example, may be quite useful as vapor therapy materials for application in the invention. Asthma or headache relief agents may be employed as well, including both "over-the-counter" and prescription vapor therapy compositions, each of which should be used only under the supervision of a physician. Essentially any composition that is effectively absorbed in the lining of the nasal passages, or is soothing when applied to the face or skin in combination with warm water vapor, can be employed in the practice of the invention.

The cushion 20 may be provided in a variety of sizes or shapes. For example, the cushion 20 may be square, rectangular, triangular, or octagonal. It may be configured in fancy or whimsical shapes. In one useful embodiment, the cushion 20 is round in shape, and is about 11 inches in diameter. The cushion could range from about 5 inches up to as much as 15 inches or greater in diameter or length.

The amount of water absorbing material 41 within the inner space of the vapor permeable cover is typically between about 0.5 lbs. and 1 lb. In one preferred embodiment of the invention, the amount of water absorbing material used is 0.75 lbs. of Pig®) Lite-Dri® absorbent material.

It is understood by one of ordinary skill in the art that the present discussion is a description of exemplary embodiments only, and is not intended as limiting the broader aspects of the present invention, which broader aspects are embodied in the exemplary constructions. The invention is shown by example in the appended claims.

What is claimed is:

1. A cushion adapted to release therapeutic vapors, said cushion comprising:
   (a) a vapor permeable cover, said vapor permeable cover enclosing an inner space and having an outer surface, said vapor permeable cover being permeable to microwaves;
   (b) a cellulose-containing absorbent material positioned within said inner space, said cellulose-containing absorbent material being capable of water uptake at ambient temperatures and water vapor release upon application of energy to said cellulose- containing absorbent material;
   (c) a vapor permeable pouch having an outer surface and having a selectively releasable connection with said vapor permeable cover, said vapor permeable pouch having an inner surface configured for receiving solid or liquid vapor therapy materials, said vapor permeable pouch being permeable to water vapor released through said vapor permeable cover into said vapor permeable pouch and adapted for releasing said vapor therapy materials in a gaseous therapeutic vapor; and
   (d) a fastener located between said outer surface of said vapor permeable pouch and said outer surface of said vapor permeable cover, said fastener permitting said connection between said vapor permeable pouch and said vapor permeable cover.

2. The cushion of claim 1, wherein said vapor permeable cover is comprised of a porous textile fabric.

3. The cushion of claim 1, wherein said vapor permeable pouch is comprised of a porous textile fabric.

4. The cushion of claim 1, wherein said fastener includes a first component configured for attachment to said vapor permeable pouch and a second component configured for attachment to said outer surface of said cover, said first component and said second component being adapted to interconnect in mating said vapor permeable pouch to said vapor permeable cover, said first and said second components being capable of selective disengagement.

5. A cushion adapted to releasee therapeutic vapors, said cushion comprising:

(a) vapor permeable cover, said vapor permeable cover enclosing an inner space and having an outer surface, said vapor permeable cover being permeable to microwaves;

(b) a cellulose-containing absorbent material positioned within said inner space, said cellulose-containing absorbent material being capable of water uptake at ambient temperatures and water vapor release upon application of energy to said cellulose- containing absorbent material;

(c) a vapor permeable pouch connected to said vapor permeable cover, said vapor permeable pouch having a surface configured for receiving solid or liquid vapor therapy materials, said vapor permeable pouch being permeable to water vapor released through said vapor permeable cover into said vapor permeable pouch and adapted for releasing said vapor therapy materials in a gaseous therapeutic vapor; and (d) a fastener, said fastener having a first component configured for attachment to said vapor permeable pouch and a second component configured for attachment to said outer surface of said cover, said first component and said second component being adapted to interconnect in mating said vapor permeable pouch to said vapor permeable cover, and said first and said second components being capable of selective disengagement; and said fastener comprising a hook and loop fastener, one of said first and second components being comprised of hook material and the other of said first and second components being comprised of loop material.

6. A cushion adapted to release therapeutic vapors, said cushion comprising:

(a) a vapor permeable cover, said vapor permeable cover enclosing an inner space and having an outer surface, said vapor permeable cover being permeable to microwaves;

(b) a cellulose-containing absorbent material positioned within said inner space, said cellulose-containing absorbent material being capable of water uptake at ambient temperatures and water vapor release upon application of energy to said cellulose-containing absorbent material;

(c) a vapor permeable pouch connected to said vapor permeable cover, said vapor permeable pouch having a surface configured for receiving solid or liquid vapor therapy materials, said vapor permeable pouch being permeable to water vapor released through said vapor permeable cover into said vapor permeable pouch and adapted for releasing said vapor therapy materials in a gaseous therapeutic vapor; and (d) a fastener, said fastener having a first component configured for attachment to said vapor permeable pouch and a second component configured for attachment to said outer surface of said cover, said first component and said second component being adapted to interconnect in mating said vapor permeable pouch to said vapor permeable cover, said first and said second components being capable of selective disengagement; and said fastener comprising a snap device, said snap device having a first portion and a second portion, one of said first and second portions being attached to said vapor permeable cover, and the other of said first and second portions being attached to said vapor permeable pouch, said first and second portion being adapted for selective mating engagement.

\* \* \* \* \*